United States Patent [19]
Schaffer

[11] Patent Number: 4,482,323
[45] Date of Patent: Nov. 13, 1984

[54] DENTAL RESTORATIONS USING NOVEL PALLADIUM SILVER ALLOY CASTING

[75] Inventor: Stephen P. Schaffer, Bloomfield, Conn.

[73] Assignee: The J. M. Ney Company, Bloomfield, Conn.

[21] Appl. No.: 381,551

[22] Filed: May 24, 1982

Related U.S. Application Data

[62] Division of Ser. No. 174,759, Aug. 4, 1980, Pat. No. 4,350,526.

[51] Int. Cl.³ .............................................. A61C 13/08
[52] U.S. Cl. ................................................... 433/207
[58] Field of Search ................ 433/207; 420/463, 464, 420/580, 587, 589

[56] References Cited

U.S. PATENT DOCUMENTS 3,929,474 12/1975 Ingersoll ............................. 420/463
3,929,475 12/1975 Ingersoll ............................. 420/505

Primary Examiner—R. Dean

[57] ABSTRACT

A dental restoration includes a casting of a palladium/silver alloy which comprises 45–60 percent palladium, 25–45 percent silver, 3–15 percent tin and/or indium, 0.3–9.0 percent zinc, 0.1–1.0 percent silicon, up to 0.25 percent rhenium and/or iridium, and up to 5 percent in total of one or more of copper, magnesium, gallium and ruthenium. The dental restorations obtained by firing porcelain against castings of this alloy exhibit freedom from discoloration, and excellent bond strength is are obtained between the porcelain coating and the underlying alloy casting.

4 Claims, No Drawings

DENTAL RESTORATIONS USING NOVEL PALLADIUM SILVER ALLOY CASTING

CROSS REFERENCE TO RELATED APPLICATION

The present application is a division of copending application Ser. No. 174,759 filed Aug. 4, 1980, now U.S. Pat. No. 4,350,526 granted Sept. 21, 1982.

BACKGROUND OF THE INVENTION

As is well known, dental casting alloys should provide a high degree of biocompatibility or inertness to the conditions in the mouth and good physical properties so that they will provide long lived usage. In addition, those alloys which are used to provide castings upon which porcelains may be cast must provide good bonding characteristics to the porcelains and other characteristics which are compatible with the porcelain, such as similar coefficient of expansion, avoidance of discoloration of the porcelain, etc. Lastly, the alloy should process well during casting and work with commercially available porcelains.

Until recent years, gold alloys, usually gold/platinum alloys, have been preferred as dental casting materials because they have provided a highly desirable balance of properties. The commercially available dental porcelains have been formulated so as to be compatible therewith.

Recently, the escalating costs of gold and platinum have resulted in extensive efforts to find alternate alloy compositions which would afford acceptable properties at considerably lower cost. Base metal alloys have generally been found to suffer from one or more limitations such as lack of sufficient biocompatibility, lack of aesthetics, etc. As a result, over the last several years, there has been considerable activity in the development of palladium base alloys and palladium/silver alloys in an effort to make use of the nobility of lower cost palladium. The silver has generally served to reduce cost still more and modify the thermal coefficient of expansion.

As a result, palladium/silver alloys have been developed which simulate the appearance of platinum alloys and which provide a high degree of biocompatibility with useful casting and physical properties. However, the silver content has a tendency to oxidize at the firing temperature and to discolor the porcelains which are fired thereon to provide the aesthetic coatings which are widely employed, particularly with anterior dental restorations.

It is an object of the present invention to provide a dental restoration using a casting of a novel palladium/silver dental alloy which is especially adapted for use with dental porcelains cast there against and which exhibits a highly desirable balance of casting properties, physical properties, biocompatibility and freedom from discoloration of porcelain coatings which are fired thereon.

It is also an object to provide such restorations using an alloy which is relatively low cost when compared to gold and platinum alloys and which alloy affords properties which are comparable thereto.

SUMMARY OF THE INVENTION

It has now been found that the foregoing and related objects may be readily attained a dental restoration having a porcelain coating upon at least a portion of a casting of a palladium/silver alloy which consists essentially of, on a weight basis, 45-60 percent palladium, 30-45 percent silver, 3-11 percent of a hardening and oxidizing component selected from the group consisting of tin, indium and mixtures thereof, 0.3-9.0 percent zinc, and 0.1-1.0 percent silicon to substantially eliminate discoloration of the porcelain coating fired there against. In addition, the alloy may optionally contain up to 0.5 percent by weight of a grain refining component selected from the group consisting of rhenium, iridium and mixtures thereof, and up to 5.0 percent of a modifying component selected from the group consisting of copper, magnesium, gallium, ruthenium and mixtures thereof. The porcelain coating of the dental restoration is substantially free from discoloration and is firmly bonded to the casting.

Preferably, the alloys have a zinc content of 0.6-1.5 percent and utilize tin as the hardening and oxidizing component in an amount of 7-10 percent by weight. Desirably, the silicon content is 0.1-0.5 percent.

DETAILED DESCRIPTION OF THE PREFERRED EMBODIMENT

As hereinbefore indicated, the alloys of the present invention do not utilize gold or platinum and use palladium as the principal component and silver as a substantial component. The alloys essentially contain a hardening and oxidizing component, zinc and silicon. In addition, they may contain as grain refining components rhenium and/or iridium and they may also contain one or more of several specified modifying metal components.

The alloys must contain at least 45 percent palladium and may contain as much as 60 percent palladium. Preferably, the alloy contains 52-58 percent palladium in order to obtain the desired nobility and an optimum balance of properties. Amounts above 60 percent significantly increase the cost and tend to adversely affect the balance of properties.

The silver content may vary from 25 to 45 percent by weight of the total composition and is preferably in the range of 30-40 percent by weight. Amounts in excess of 45 percent by weight significantly increase the tarnish characteristics of the alloy and the tendency towards discoloration of the porcelain, and they also tend to adversely affect the thermal expansion which must be compatible with that of the porcelain to be fired thereon.

To provide both hardness to the alloy and the necessary oxide formation to effect bonding with the porcelain coating, tin, indium or the combination thereof must be used in an amount of 5-15 percent and preferably in the range of 7-11 percent. Amounts above 15 percent will overly harden the alloy and tend to adversely affect other properties.

Zinc is added in the range of 0.3-9.0 percent and preferably in the range of 0.5-1.5 in order to provide the desired fluidity and ductility, and to enhance hardening and otherwise contribute to the desired balance of properties for the alloy.

The last essential component comprises silicon which has the effect of preventing discoloration of the porcelain during firing. Its effect is not fully understood but amounts of as little as 0.1 percent have been found to provide significant benefits. Generally, amounts in excess of 0.5 percent provide no additional benefit, and amounts in excess of 1 percent adversely affect the balance of properties of the alloy and should not be employed. Preferably, silicon is used in the amount of 0.2–0.5 percent.

For some applications, it may be desirable to incorporate rhenium and/or iridium in the amount of up to 0.5 percent by weight in order to effect grain refinement. When such a grain refining component is included, it is preferably in the range of 0.05–0.15 percent. However, desirable casting and other properties have been obtained without the incorporation of a grain refining component.

In some applications, it may be desirable to add one or more modifiying metals from the group comprising copper, magnesium, gallium and ruthenium. Magnesium and ruthenium, when used in combination, exhibit some effect in eliminating discoloration and thus would cooperate with the silicon in this regard, while minimizing the hardening that would otherwise occur by increasing amounts of silicon. Gallium functions as an oxidizer to provide the bonding of the porcelain thereto and therefore can replace a portion of the tin or indium component. Copper functions as a hardener in the alloy and may replace a portion of the tin or indium if this is desired. Such optional modifying metals should not comprise more than 5 percent of the alloy in total and preferably should be present in a total amount of less than 3 percent.

The alloys produced in accordance with the present invention routinely exhibit a hardness in excess of 150 Vickers, which is necessary to withstand the abrasion of opposing teeth; however, a hardness of 300 or more is undesirable because of the tendency to wear the opposing teeth. Because the porcelain coating is fired at about 1000° Centigrade, the solidus temperature must be in excess of 1100° Centigrade. The liquidus temperature of the alloy is well below 1400° Centigrade to permit facile processing in the equipment generally available in dental laboratories. To provide a good compatible alloy for use with present commercial porcelains, the alloy has a coefficient of thermal expansion within the range of 0.66–0.72 percent at 500° Centigrade. The tensile elongation of the alloy is in excess of 6 percent to permit the margins of the casting to be adjusted in the mouth of the patient. Significantly, the alloys of the present invention have both high corrosion resistance and tarnish resistance and they do not discolor the porcelain. The mechanism of the porcelain discolorations is not fully understood but is believed to result from the formation of silver oxide during firing of the porcelain and the diffusion of the silver oxide into the porcelain coating where it undergoes ion exchange with the sodium. This produces significant discoloration of the porcelain. The small amounts of silicon in the present alloy eliminate this problem.

Illustrative of the efficacy of the alloys of the present invention are the following examples, wherein all parts are parts by weight unless otherwise indicated:

EXAMPLE ONE

An alloy is prepared containing 55 percent palladium, 35 percent silver, 9 percent tin, 1 percent zinc and 0.2 percent silicon.

The alloy is determined to have a solidus temperature of 1180° Centigrade and a liquidus temperature of 1260° Centigrade. Specimens cast therefrom are found to exhibit a Vickers hardness of 241 and to have an offset yield strength at 0.1 percent of 67,700 p.s.i. The tensile elongation is 18 percent and the coefficient of thermal expansion at 500° Centigrade is 0.72 percent.

Several commercial porcelains available from different manufacturers are fired against castings of this alloy in accordance with the manufacturers' specifications. In all instances, the bond strength ratio (maximum bending stress/modulus of elasticity of the alloy) is found to exceed 1.1 and the maximum bending stress is found in all instances to exceed 21,900 p.s.i.

The fired restorations are found to be free from any discoloration of the porcelain and exposure to corrosion testing indicates freedom from tarnish.

EXAMPLE TWO

To illustrate the effect of omitting the silicon component, an alloy formulation was prepared and cast with all other components of the alloy as set forth in Example One. A commercial porcelain was fired thereagainst in accordance with the recommendations of the manufacturer.

Although the physical properties of this alloy were comparable to those of the alloy of the present invention containing the silicon addition, significant discoloration was found in the porcelain coatings fired thereon.

EXAMPLE THREE

To illustrate the effect of varying the amounts of silicon from the levels set forth in Example One, two additional formulations were prepared, the first containing only 0.1 percent silicon and the second containing 0.3 percent. The remaining components were as set forth in Example One. The physical properties of specimens cast from these alloys are set forth in the table below, as are the observations with respect to discoloration of the fired porcelain coatings produced thereon:

| Property | Alloy Containing 0.10% | Alloy Containing 0.30% |
|---|---|---|
| Vickers Hardness | 241 | 249 |
| Tensile Elongation, % | 14 | 8 |
| Thermal Expansion | .73 | .72 |
| Offset Yield Strength at 0.1% | 67,700 | 62,000 |
| Discoloration of Porcelain | very slight | none |
| Tarnish | none | none |

It can be seen that increasing the silicon content without adjustment of other components will tend to harden the alloy while continuing to effect the desired elimination of discoloration of the porcelain coating.

Thus, it can be seen from the foregoing detailed specification and examples that the dental restorations using the alloys of the present invention exhibit a highly desirable balance of properties and that the alloys exhibit good casting characteristics, good physical properties, high tarnish resistance, solderability, sufficient ductility to facilitate working, and most importantly, substantial elimination of any tendency for discoloration of porcelain coatings fired thereon. The alloys may be processed readily using available dental laboratory equipment and readily lend themselves for use with currently available commercial porcelains. The result is highly attractive, useful and long lived dental restorations.

Having thus described the invention, I claim:
1. A dental restoration comprising:
   A. a casting of an alloy consisting essentially of:
      (1) 45–60 percent by weight palladium;
      (2) 25–45 percent by weight silver;

(3) 3–15 percent by weight of a hardening and oxidizing component selected from the group consisting of tin, indium and mixtures thereof;
(4) 0.3–9.0 percent by weight zinc;
(5) 0.1–1.0 percent by weight silicon to substantially eliminate discoloration of the porcelain coating fired thereagainst;
(6) up to 0.5 percent by weight of a grain refining component selected from the group consisting of rhenium, iridium and mixtures thereof; and
(7) up to 5.0 percent by weight of a modifying component selected from the group consisting of copper, magnesium, gallium, ruthenium and mixtures thereof; and B. a porcelain coating upon a portion of said casting, said porcelain coating being substantially free from discoloration and firmly bonded to said casting.

2. The dental restoration of claim 1 wherein the zinc content is 0.6–1.5 percent by weight.

3. The dental restoration of claim 1 wherein the hardening and oxidizing component is tin in the amount of 7.0–10.0 percent by weight.

4. The dental restoration of claim 1 wherein the silicon content is 0.1–0.5 percent by weight.

* * * * *